United States Patent [19]

Fildes et al.

[11] Patent Number: 4,786,220
[45] Date of Patent: Nov. 22, 1988

[54] CUTTING TOOL WEAR MONITOR

[75] Inventors: John M. Fildes, Hanover Park; Robert H. Krueger, Palatine, both of Ill.

[73] Assignee: Borg-Warner Corporation, Chicago, Ill.

[21] Appl. No.: 53,643

[22] Filed: May 26, 1987

Related U.S. Application Data

[62] Division of Ser. No. 832,616, Feb. 24, 1986, Pat. No. 4,694,688.

[51] Int. Cl.[4] .......................... B23C 7/00; B23B 49/00
[52] U.S. Cl. ...................................... 409/134; 408/11; 409/194
[58] Field of Search ....................... 409/134, 194, 187; 340/679, 680; 73/104; 408/2, 6, 11

[56] References Cited

U.S. PATENT DOCUMENTS

| | | | |
|---|---|---|---|
| 2,978,689 | 4/1961 | Tech et al. | 408/6 |
| 3,001,421 | 9/1961 | Martens | 408/6 X |
| 3,299,697 | 1/1967 | Sparling | 408/6 X |
| 3,310,796 | 3/1967 | Sanders | 408/6 |
| 3,694,637 | 9/1972 | Edwin et al. | 73/104 |
| 3,747,085 | 7/1983 | Bala et al. | 408/6 X |
| 3,793,627 | 2/1974 | Darrel et al. | 73/104 |
| 3,809,870 | 5/1974 | Auble et al. | 73/104 X |
| 3,990,805 | 11/1976 | Ducrohet | 408/6 |
| 4,087,801 | 5/1978 | Noh | 73/104 X |
| 4,090,403 | 5/1978 | Tsukada et al. | 73/104 |
| 4,203,691 | 5/1980 | Nishimura et al. | 408/2 |
| 4,207,567 | 6/1980 | Juengel et al. | 73/104 X |
| 4,326,257 | 4/1982 | Sata et al. | 73/104 X |
| 4,329,771 | 5/1982 | Eto et al. | 408/6 |
| 4,338,556 | 7/1982 | Hetzel | 408/11 |
| 4,396,322 | 8/1983 | Nomura et al. | 409/134 |
| 4,442,494 | 4/1984 | Fromson et al. | 73/104 X |
| 4,564,911 | 1/1986 | Smith et al. | 73/104 X |

FOREIGN PATENT DOCUMENTS

| | | | |
|---|---|---|---|
| 3136434 | 3/1983 | Fed. Rep. of Germany | 73/104 |
| 52-282 | 4/1977 | Japan | 73/104 |
| 14135 | 2/1981 | Japan | 73/104 |
| 494656 | 2/1976 | U.S.S.R. | 73/104 |

OTHER PUBLICATIONS

Dr. H. Bagchi, "Fine Machining and Thermoelectric Wear", Industrial Lubrication and Tribology, Jul.-/Aug. 1980, pp. 124 & 125.
H. Bagchi et al., "Thermoelectric Wear in Tools", Wear, vol. 26, 1983, pp. 39–44.
H. S. Shan et al., "Wear of Cutting Tools: Thermo-Electric Effects", Wear, vol. 32, 1975, pp. 167–179.
L. J. Bredell, "The Influence of Thermoelectric Current on the Wear of Tungsten Carbide Tools", Sci. Hard Matr. Pro. Inter. Conf., Plenum, N.Y. 1983, pp. 723–734.
N. Gane, "Thermoelectric Effects During the Frictional Sliding and Cutting of Metals", Wear, vol. 86, 1983, pp. 167–172.
S. A. Hoenig et al., "Monitoring Drill Wear Electrically", Machine Design, Dec. 8, 1983, pp. 174–175.

*Primary Examiner*—William R. Briggs
*Attorney, Agent, or Firm*—James A. Geppert

[57] ABSTRACT

A method and apparatus by which the degree of wear and useful life limitations of a drill, end mill or other types of metal removal tools can be detected. The method is based on the short circuit current, open circuit voltage and/or power that is generated during metal removal by the utilization of an insulated rotary tool bit to which electrical contact is made by a non-rotating conductor and an insulated or non-insulated workpiece, with an external circuit connecting the tool and workpiece through a measuring device. The generated current, voltage or power shows a sharp increase or change in slope upon considerable tool wear and/or at the point of failure.

7 Claims, 6 Drawing Sheets

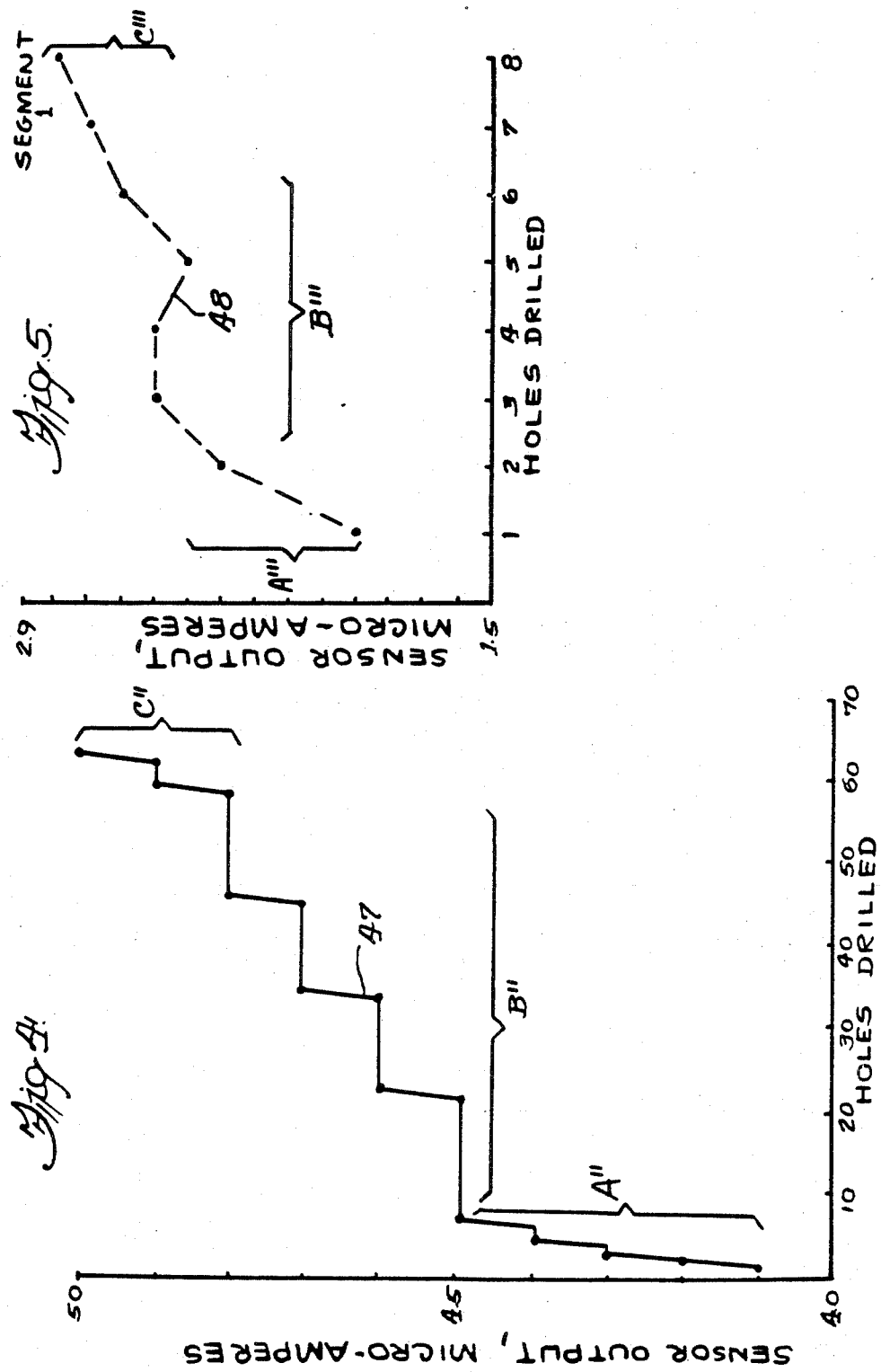

CUTTING TOOL WEAR MONITOR

This is a division of application Ser. No. 832,616 filed Feb. 24, 1986, now U.S. Pat. No. 4,694,686.

BACKGROUND OF THE INVENTION

Tool wear has an important bearing on the performance of metal removal operations, where worn tools may result in scrapped workpieces due to unacceptable surface finish, out of tolerance dimensions, or damage caused by tool breakage. For these reasons, it has become common practice in machining operations to replace a cutting tool long before the end of its useful life, resulting in poor utilization of tools. Thus, there is the need for an effective method of measuring the amount of wear on a tool while cutting is in operation. At the present time, an acceptable tool wear sensing technology does not appear to exist.

Technologies have been and are being explored for monitoring cutting tool wear based on fundamental features and phenomena of wear and failure mechanisms that have been observed during cutting operations. Briefly, three distinct failure mechanisms have been identified:

1. Gross plastic deformation caused by excessively elevated temperatures.
2. Fatigue caused by excessively large cutting forces.
3. Gradual wear caused by the processes of adhesion, abrasion, electrochemical conversion and atomic diffusion.

The wear and failure mechanism that occurs in a specific situation depends on the cutting forces, temperature, and the tool and workpiece materials (e.g. composition, grain structure, surface composition). The variety of wear and failure mechanisms have resulted in various modes of testing and monitoring.

One such measurement involves the dimensional changes of the cutting tool or workpiece. This class of techniques includes mechanical gauging, profile tracers, weighing, ultrasonics, optical comparator methods and radiotracer methods. Except for radiotracer methods, all of these techniques are off-line measurements that frequently miss detection of the approach to failure. Also, radioactive methods are slow and perceived as unsafe.

The reactionship between cutting forces and tool wear have been actively explored over the last twenty-five years, but a general correlation has not been established. For example, progressive flank wear produces increasing forces whereas progressive crater wear has the opposite effect. The observed forces also depend on material hardness, depth of cut and cutting speed. These techniques are hard to implement; requiring careful placement of strain gauges or dynometers. Transducers frequently have to be incorporated into the original design of the machine.

Measurement of power consumption by the spindle or feed motor of a matchining tool is easy to implement on new or existing machines. Such techniques have the potential of providing real-time optimization of metal removal rates, but serious disadvantages are inherent in these methods. Wear produces very small changes in power consumption which must be detected as a perturbation of a much larger signal (e.g. the overall power consumption of the motor). These methods are sensitive to non-wear related factors. Progressive wear of the tool increases power consumption but plastic deformation of the tool at high temperature decreases power consumption.

The bulk temperature of a tool can be measured by an embedded thermocouple or infrared technique. Infrared measurement has the disadvantage of requiring a very clean environment not found on a machine production floor, while embedded thermocouples require extensive redesign of a machine's spindle. The rise in the bulk temperature of the tool, caused by wear, is very small and the signal to noise ratio is poor.

Currently, vibration and sound analysis are active research areas, possibly because of the successful application of these methods to the study of rotating machinery and crack propagation in ceramics. The results of such analysis are very specific to a particular set-up and hard to generalize, and the techniques are difficult to implement, expensive and difficult to utilize. Therefore, a number of different techniques have been tried over the years with little success in the predictability of excess tool wear and/or failure. The present invention overcomes the deficiencies of previous techniques to provide an effective tool wear monitoring technique.

SUMMARY OF THE INVENTION

The present invention relates to a novel method for monitoring wear of a rotating cutting tool based on short circuit current, open circuit voltage and/or power generated during the cutting operation on a workpiece. As the tool wears, the generated current, voltage or power gradually increases until a generally sharp increase signifies failure of the tool due to excessive wear or breakage.

The present invention also relates to the provision of an apparatus for monitoring tool wear in drilling, milling or other machining or metal removal operations wherein the electrical resistance along a path from the tool to the measuring circuit input for the workpiece must be much less than any other potential electrical path. Depending on the machine tool, both tool and workpiece might need to be insulated, neither might require insulation, or one, but not both, might require insulation. A non-rotating contact for the tool can be utilized where it provides low electrical resistance.

The present invention further relates to a method of predicting tool failure for a metal removal tool based on the material being worked on, the elapsed time of use of the tool and the current being generated by the metal removal operation. Tool failure may be detected by a comparison of the observed generated current to the predicted current for failure or based on the derivative of the observed current, i.e. the slope change in a graph of generated current vs. time. Also, a low impedance current measurement is utilized to reduce error in the system from utilization of the current to provide a reading thereof.

Further objects are to provide a construction of maximum simplicity, efficiency, economy and ease of assembly and operation, and such further objects, advantages, and capabilities as will later more fully appear and are inherently possessed thereby.

DESCRIPTION OF THE DRAWINGS

FIG. 4 is a graph similar to FIG. 2, but for large hole drilling.

FIG. 5 is a graph similar to FIG. 2, but for deep hole drilling.

DESCRIPTION OF THE PREFERRED EMBODIMENT

Figure 1:
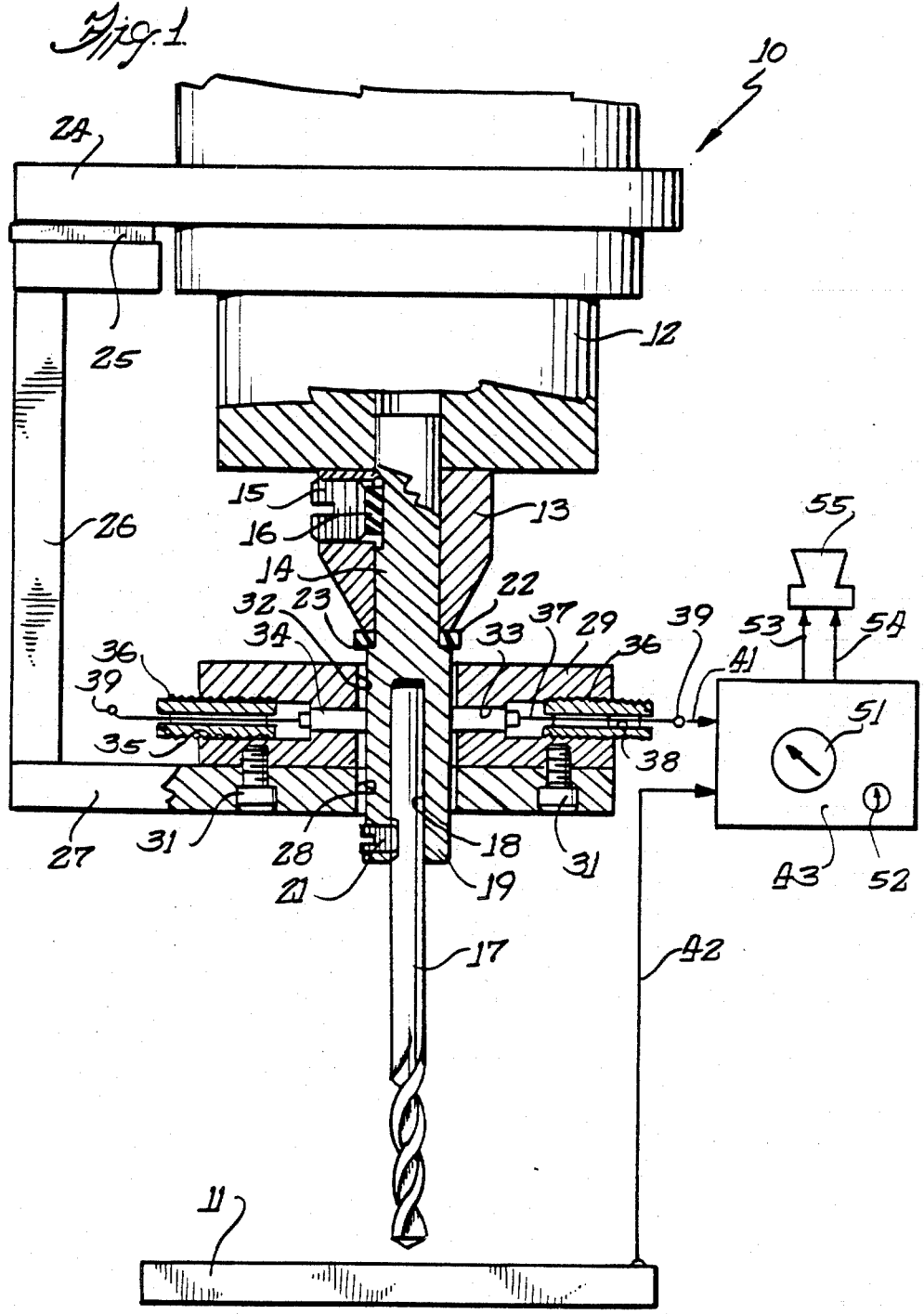
FIG. 1 is a combined schematic and sectional showing of the cutting tool wear monitoring apparatus applied to a drilling machine tool.

Referring more particularly to the disclosure in the drawings wherein is shown an illustrative embodiment of the present invention, FIG. 1 discloses a machine tool 10 utilized for the drilling of holes in a workpiece 11 wherein the machine includes a machine head 12 having a rotating collet 13 mounted therein for rotation by a motor (not shown). A collet insert or drill holder 14 may have a shrink plastic tubing thereon to insulate the holder from the collet 13; a set screw 15 and insulator 16 being mounted in the collet to further secure the holder therein. A drill 17 is received in a blind passage 18 in the lower end 19 of the holder and a set screw 21 retains the drill therein for rotation by the machine. An insulating washer 22 encompasses the holder 14 between the end of the collet 13 and a shoulder 23 on the holder.

Mounted on the machine head 12 is a platform 24 having a depending bracket 26 secured thereto and insulated therefrom by an insulator 25. A horizontal arm 27 on the bracket 26 extends laterally to the axis of the holder 14 and has an opening 28 therein through which the drill holder projects. An annular phenolic brush holder 29 is secured to the arm 27 by retaining screws 31 and has a central opening 32 axially aligned with the opening 28 in the arm. The holder 29 has a plurality of circumferentially spaced radially extending passages 33, each passage receiving a brush assembly 34 that is in electrical contact with the lower portion 19 of the drill holder 14. Each passage 33 has an enlarged threaded outer portion 35 to receive a nylon brush retainer screw 36. A lead 37 extends through a central opening 38 in each screw 36 and is connected to the outer end of the brush assembly 34, the opposite end of each lead terminating in a brush connector ring 39.

All of the connector rings 39 are connected to a lead 41, and a second lead 42 is connected to the workpiece; with the leads 41 and 42 being connected to a suitable measuring device 43 having a circuit that will provide measurement of voltage, current and/or power. This device would also have predictive functions from a generated signal. The device 43 receiving the leads 41,42 includes an indicator dial 51 showing the level of the generated current, voltage and/or power and a knob 52 is provided to adjust the level of current at which a signal will be passed through leads 53,54 to an indicating means 55 to indicate that the tool has reached a threshold voltage, current or power condition with a change in slope indicating approaching failure. The means 55 is shown as a speaker to provide an audible signal to the machine operator, although a visual signal, such as a signal light would also be appropriate. In the alternative, the signal that is emitted from the device 43 could result in an automatic shut-down of the tool without intervention by the operator.

For the predictive functions, a means for monitoring the machining time is included in the device 43. The method of measuring the current and/or voltage may also be important. For instances that produce uniform wear of all cutting edges of the tool, a measurement of the average voltage and/or current is sufficient. However, where uniform wear is not produced on all of the cutting edges, average measurements may not be sufficient, and measurement of the voltage and/or current generated by each cutting edge may be required. This could be performed by very rapid data acquisition that is synchronized with the rotational frequency of the edges. An easier alternative might be the rapid collection of a set of non-synchronized measurements; wherein some measurements in the set will have contributions from more than one cutting edge, but some of the measurements will have a predominant contribution from a single edge. As increased wear generates larger voltages and currents, the largest value in the set of measurements, therefore, should have come from the most worn edge.

Although the tool 17 and workpiece 11 are shown as requiring insulation, the important factor to be considered is that the electrical resistance along a path from the tool 17 to the measuring circuit input to the workpiece must be less (e.g. 100 or more times less) than any other potential electrical path. Depending upon the machine tool, especially the electrical resistance of the spindle bearings, both tool and workpiece may need to be insulated, neither may need insulation, or one, but not both, may need to be insulated. Obviously, it is preferable not to have to insulate either one.

The design of the rotating contact for the tool or tool holder requires only that it provides low electrical resistance and little reduction of the rigidity of the tool/tool holder system. Although shown as a plurality of brushes 34 in a non-rotating ring or holder 29, a mercury slip ring or other suitable structure could also be used.

Figure 2:
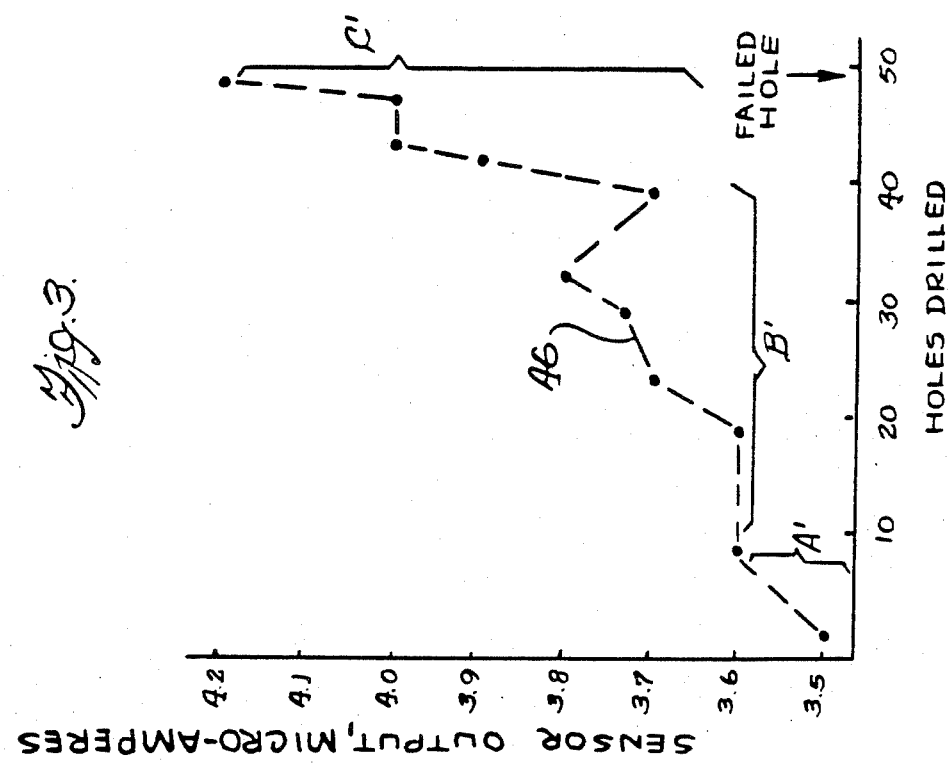
FIG. 2 is a graph showing generated current versus the number of holes drilled for a dry high speed tool steel bit.

A characteristic curve for a drilling operation is shown in the graph of FIG. 2 where the generated current is plotted versus the number of holes drilled by a high speed tool steel bit in the dry drilling of 01 tool steel workpieces. The curve 45 has an initial steep slope A which then generally levels off in area B and finally reaches a steep incline C at the point of threshold current indicating near tool failure. The drill had a 0.25 inch bit rotated at a speed of 1150 rpm with a feed of 0.006 inch per revolution and a detph of 0.375 inch. The current amplitude at the onset of failure increases by 50 to 100% compared to the average current level over the B area of the graph and may occur over an extremely short period of time.

Figure 3:
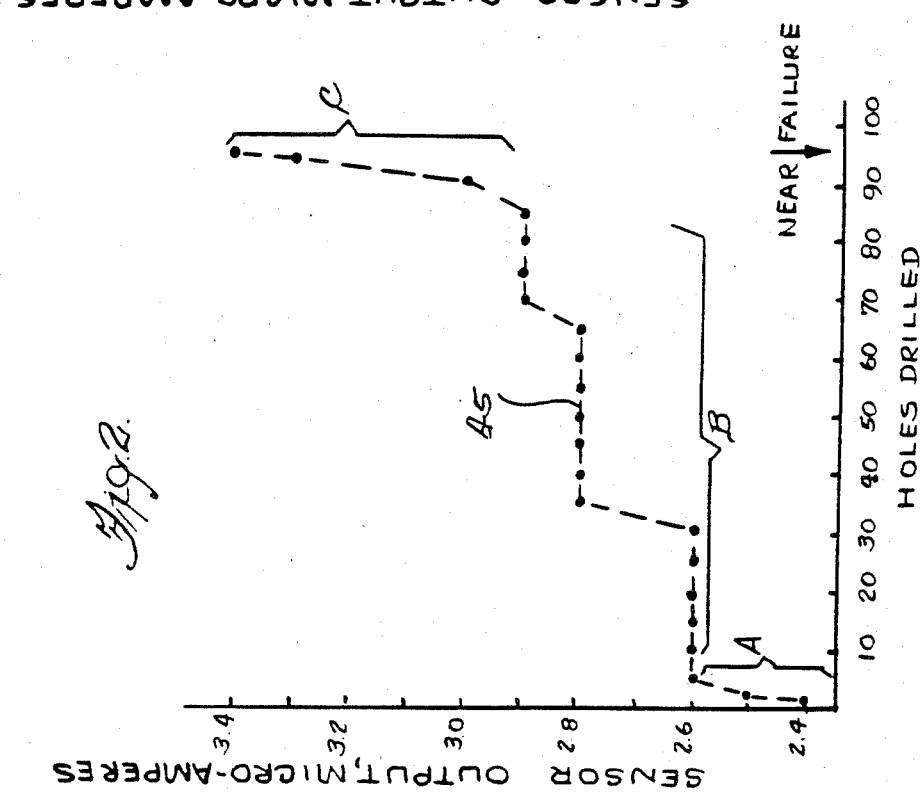
FIG. 3 is a graph similar to FIG. 2 except for a dry oxide coated high speed tool steel bit.

FIG. 3 shows an illustrative graph for the dry drilling of an 01 tool steel workpiece with an oxide coated high speed tool steel bit. Here again, an initial steep incline A' of curve 46 is followed by a generally lateral line B' and finally a sharp incline C' to failure. Similar results are obtained in dry drilling of steel utilizing an oxide coated tool steel bit, and similar results occur with the drilling of stainless steel. A lubricated cutter tool works as well as a dry cutting tool for the monitoring FIG. 4 illustrates a graph for a large hole drilling operation using a 0.75 inch high speed tool steel bit on a 01 tool steel workpiece at 800 rpm for a hole depth of 0.375 inch with a feed of 0.003 inch per revolution. Here again there is an initial steep incline A″ of curve 47, a lateral stepped area B″ and a final steep incline C″ to approximate tool failure.

FIG. 5 shows a graph illustrating generated current versus the number of holes drilled to a constant depth for deep hole drilling. A 0.25 inch oxide coated tool bit is rotated 800 rpm and fed at 0.003 inch per revolution acting on a 01 tool steel workpiece for a depth of 2.0 inch. As seen the initial incline A‴ of curve 48 and final incline C‴ are not as steep as those for shallower holes, but the final incline appears indicative of a threshold current predicatable of tool failure.

All of the previous graphs illustrate the indication of catastrophic tool failure by a slope change of the threshold current, however, a specific degree of wear can be detected by comparison of the observed current, voltage or power to a reference value. Furthermore, the remaining life of the tool can be predicted from the observed current, voltage or power by use of a reference equation that relates the observed signal to the machining time. The form of this equation is typically $$t_{failure} = \frac{bt}{Ln(I \text{ or } V \text{ or } P) - Ln(a)}$$

where I is the observed current, V is the voltage, P is the power, t is the machining time at which the electrical parameter was observed, t failure is the predicted time of tool failure and a and b are constants that depend on the nature of the machining operation.

Figure 6:
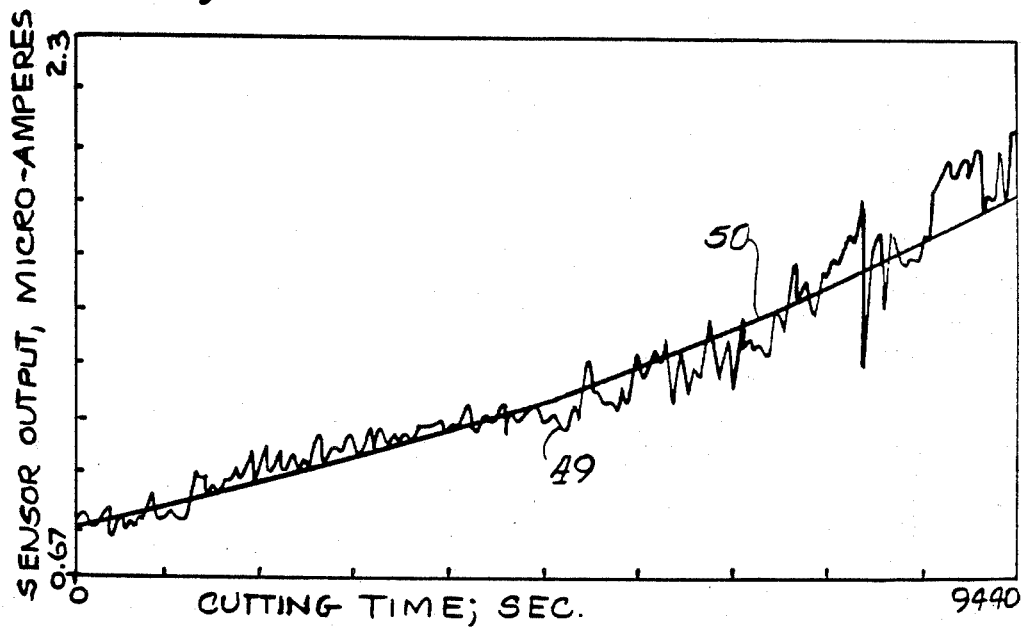
FIG. 6 is a graph illustrating average current versus time of milling for the tool in an end milling operation.

FIG. 6 illustrates a characteristic curve 49 for a milling operation utilizing a 0.25 inch high speed tool steel cutter or bit on a 01 tool steel workpiece where the bit operates at 600 rpm with a feed of 0.5 inches per minute and a 0.03 inch depth of cut. Both drilling and milling operations are typically performed on the same or similar machines, with the primary difference residing in the geometry of the tool cutting edges; i.e., the depth and height of the cutting flutes. The curve 50 superimposed over the curve 49 for the current generated is derived from the following general equation:

$$I = a \exp\left(b \frac{t}{t_{failure}}\right)$$

which equation is a more general form of the first equation for predicting tool failure. The curve 49 generally follows the curve derived from the last equation until a larger deviation is noted when the wear of the tool becomes greater and approaches tool failure.

Figure 7:
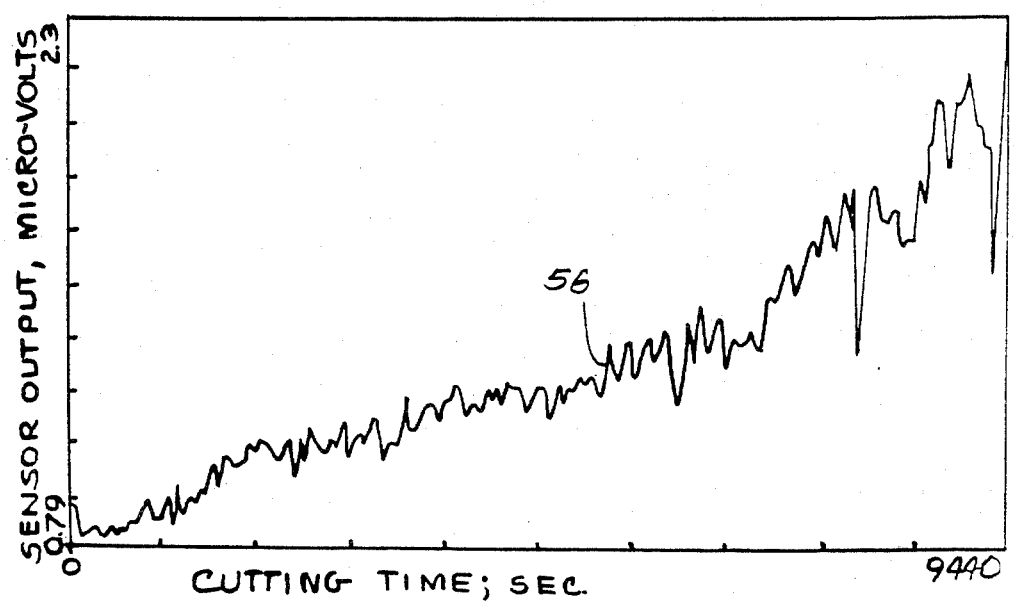
FIG. 7 is a graph similar to FIG. 6, but showing average voltage versus time of milling.

FIG. 7 is a similar curve 56 where the voltage is plotted against the elapsed time of the milling operation. This curve 56 generally corresponds to the curve 49 in FIG. 6.

Figure 8:
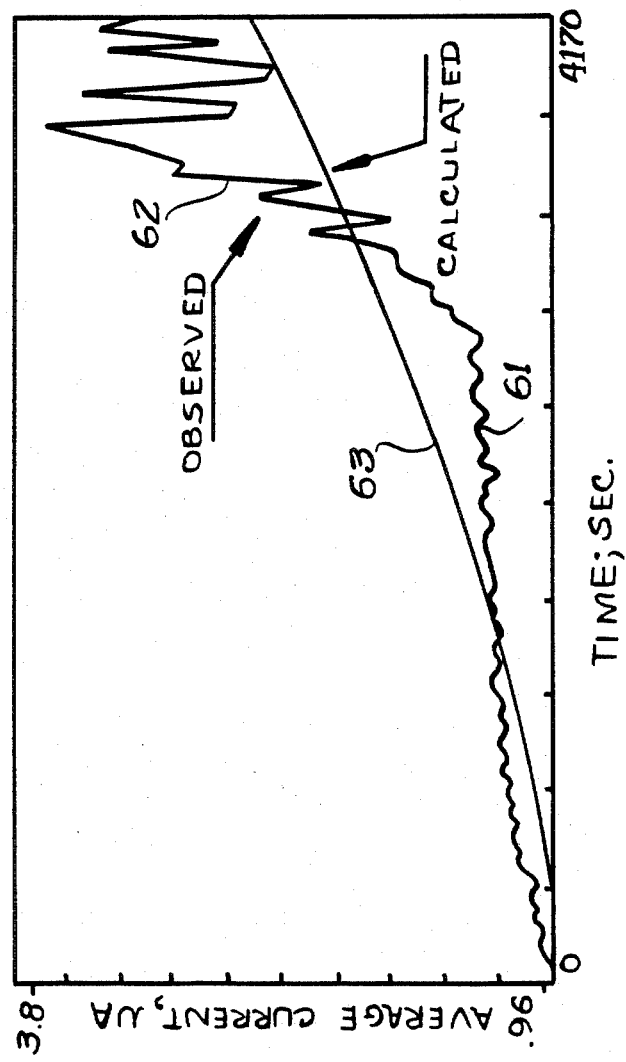
FIG. 8 is a graph illustrating a further milling operation plotting the average current output generated during metal removal versus elapsed time.

FIG. 8 is a third curve 61 where average current is plotted against the elapsed time of a milling operation and shows a sudden slope change at 62 indicative of tool wear at approximate failure condition. The smooth line 63 is indicative of the calculated current utilizing the first equation on page 10.

Figure 9:
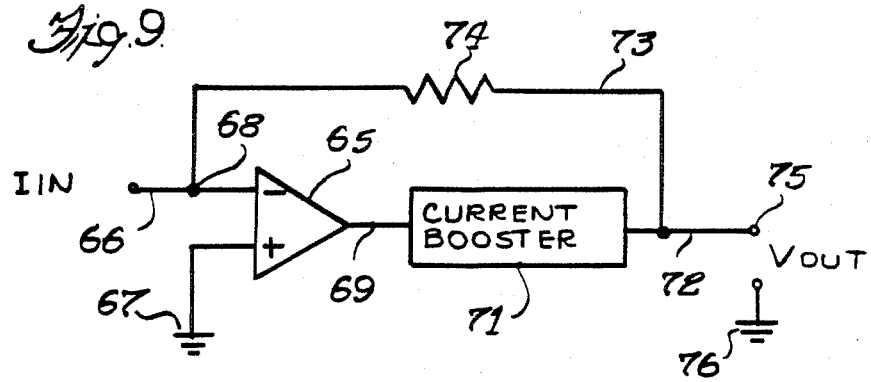
FIG. 9 is a showing of a circuit for low impedence current magnitude measurement for a cutting tool monitor.

To provide a low impedance current measurement for the current generated during the metal removal operation, a circuit is illustrated in FIG. 9 where an operational amplifier (integrated circuit) 65 has an input line 66 to the minus side for the generated current from the tool of FIG. 1 and the plus side is connected to ground 67. Likewise, the workpiece 11 engaged by the tool is grounded. Line 69 has a current booster 71 formed of a pair of transistors to boost the current sourcing capability of the amplifier 65. A feedback loop 73 containing a suitable resistance 74 extends from line 72 after the booster 71 to return to line 66. The voltage output to ground 76 across point 75 is proportional to the current input at line 66.

The amplifier 65 acts to balance the current input with the current feedback through loop 73 so the current difference at point 68 is zero. To provide a current balance, some voltage must be generated with this voltage output indicating the current input without actually using any current in the system to avoid error. Because of the zero current, this circuit provides a low impedence measurement for the tool.

Figure 10:
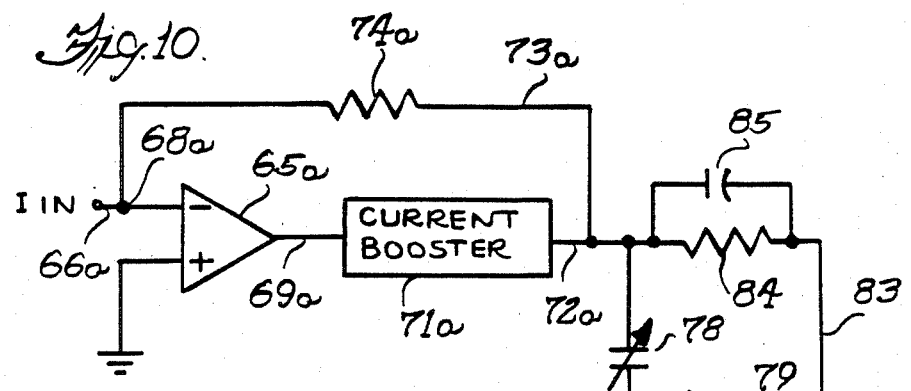
FIG. 10 is a showing of a circuit for low impedance current time derivative measurement.

Similarly, the circuit of FIG. 10 is supplemental to the circuit of FIG. 9 with like parts having the same numeral with a script "a". The operational amplifier 65a receives the current input from the tool through line 66a with the output boosted by the current booster 71a in line 69a. The feedback loop 73a containing resistance 74a leads from line 72a back to point 68a. The line 72a connects to a line 77 containing a variable capacitor 78 and leading from the output of the booster 71a to the minus side of a second operational amplifier 79; the positive side being grounded at 81. A feedback loop 83 from output 82 contains a resistance 84 and capacitor 85 in parallel and extends from output 82 on the output side of amplifier 79 to the line 72a. The voltage output at line 82 is proportion to the derivative of the current input with respect to time; i.e. the time rate of change of the current or slope.

Figure 11:
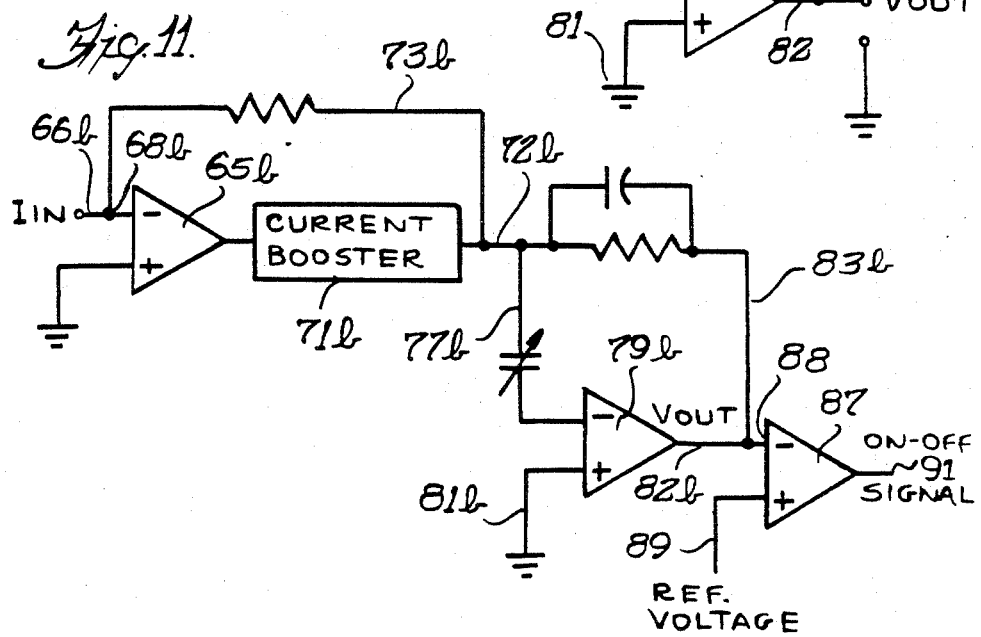
FIG. 11 is a showing of the circuit of FIG. 10 with an additional control feature.

The circuit of FIG. 10 is shown in FIG. 11 with the addition of a comparator 87, with like parts having the same numeral with a script "b". In this embodiment, the voltage output from line 82b is connected to the negative side 88 of a third operational amplifier 87 or comparator. The positive side 89 of the comparator is connected to a reference voltage corresponding to the slope change to be detected. The output 91 from the comparator provides an on-off signal to a relay for the feed motor and/or alarm for the cutting system. Obviously, the comparator 87 may be added to the circuit of FIG. 9 with the negative side 88 connected to the voltage output of line 72.

Although shown and described for use in a drilling or milling operation of metal removal, it is contemplated that the tool monitoring and failure predicting function could also be effectively utilized in other metal cutting or removing operations such as turning on a lathe or shaping, and all such metal removal operations are contemplated in the following claims.

We claim:

1. Apparatus for detecting tool wear failure in a machine for metal removal including a shaft, shaft rotating means, a tool holder secured on said shaft, a rotary tool bit mounted in said holder for engagement with a workpiece, a nonrotating holder having a central opening through which said tool bit projects, and a circuit between means contacting said nonrotating holder and means contacting said workpiece to ground to measure the current generated by metal removal of said tool bit acting on said workpiece, said circuit providing a low impedance current measurement means including an operational amplifier receiving the current input from the tool, a current booster for the output from the amplifier and a feedback loop containing a resistance and leading to the current input from the amplifier, said circuit balancing the current feedback with the current input and provides a voltage output proportional to the current input.

2. Apparatus for detecting tool wear failure as set forth in claim 1, including a second operational amplifier receiving the voltage output through a variable capacitor, and a feedback loop from the second amplifier leading to said voltage output.

3. Apparatus for detecting tool wear failure as set forth in claim 2, including a comparator receiving the voltage output from said second amplifier and providing a control for the shaft rotating and feed means.

4. Apparatus for detecting tool wear failure in a machine for metal removal including a shaft, shaft rotating means, a tool holder secured on said shaft, a rotary tool bit mounted in said holder for engagement with a workpiece, a non-rotating holder having a central opening through which said tool bit projects, and a circuit between means contacting said non-rotating holder and means contacting said workpiece to ground to measure the current generated by metal removal of said tool bit acting on said workpiece, the electrical resistance along the path from the tool bit to the measuring circuit and to the workpiece being much less than any other potential electrical path.

5. Apparatus for detecting tool wear failure as set forth in claim 4 wherein said contact means for the tool holder comprises a plurality of brush assemblies retained in said holder and in electrical contact with the measuring circuit.

6. Apparatus for detecting tool wear failure as set forth in claim 5, wherein said workpiece is insulated from said machine.

7. Apparatus for detecting tool wear failure in a machine for metal removal including a shaft, shaft rotating means, a tool holder secured on said shaft, a rotary tool bit mounted in said holder for engagement with a workpiece, a nonrotating holder having a central opening through which said tool bit projects, and a circuit between means contacting said nonrotating holder and means contacting said workpiece to ground to measure the current generated by metal removal of said tool bit acting on said workpiece, said circuit including means for predicting the time of tool failure based on the current generated at a particular elapsed time of cutting for the tool according to the following equation:

$$t \text{ failure} = \frac{bt}{\text{Ln}(I) - \text{Ln}(a)}$$

wherein
 t failure is the time to produce tool failure in seconds,
 t is the elapsed cutting time for the tool in seconds,
 I is the observed current in microamperes, and
 a and b are constants depending on the machining operation.

* * * * *